United States Patent
He et al.

(10) Patent No.: US 8,060,182 B2
(45) Date of Patent: Nov. 15, 2011

(54) MRI-MONITORED EQUIPMENT WITH BUILT-IN MR SIGNAL RECEPTION COIL AND SIGNAL EMITTER

(75) Inventors: Zeng He He, Shenzhen (CN); Jian Min Wang, Shenzhen (CN); Yang Wang, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 1161 days.

(21) Appl. No.: 11/775,286

(22) Filed: Jul. 10, 2007

(65) Prior Publication Data
US 2008/0021305 A1    Jan. 24, 2008

(30) Foreign Application Priority Data
Jul. 19, 2006    (CN) .......................... 2006 1 0088822

(51) Int. Cl.
*A61B 5/055* (2006.01)

(52) U.S. Cl. .............................. 600/411; 600/422; 601/3

(58) Field of Classification Search ................... 600/411, 600/422; 601/3
See application file for complete search history.

(56) References Cited

U.S. PATENT DOCUMENTS

| | | | |
|---|---|---|---|
| 5,590,653 A * | 1/1997 | Aida et al. ..................... 600/411 |
| 6,516,211 B1 * | 2/2003 | Acker et al. ................... 600/411 |
| 2007/0069728 A1 * | 3/2007 | Van Helvoort et al. ........ 324/318 |

* cited by examiner

*Primary Examiner* — Brian Casler
*Assistant Examiner* — Jonathan Cwern
(74) *Attorney, Agent, or Firm* — Schiff Hardin LLP

(57) ABSTRACT

In a system having a magnetic resonance imaging (MRI) apparatus and MRI-monitored medical equipment, the MRI-monitored medical equipment has an inductive coil built into the equipment that receives magnetic resonance signals from a subject and generates inductive electromagnetic signals according to the received magnetic resonance signals. The magnetic resonance imaging system has at least one reception coil that is positioned externally of the MRI-monitored medical equipment and that is connected to the magnetic resonance imaging system via a cable. The reception coil receives the electromagnetic signals that are generated by the inductive coil that is built into the medical equipment.

5 Claims, 1 Drawing Sheet

MRI-MONITORED EQUIPMENT WITH BUILT-IN MR SIGNAL RECEPTION COIL AND SIGNAL EMITTER

BACKGROUND OF THE INVENTION

1. Field of the Invention

The present invention relates to the field of magnetic resonance, particularly to the field of magnetic resonance imaging, and specifically, to an apparatus for transmitting magnetic resonance signals in MRI-monitored medical equipment.

2. Description of the Prior Art

Various forms of therapeutic treatments can be applied to the body of a human or other mammalian subject by applying energy from outside the body. For example, when treatments are performed by using hyperthermia techniques, ultrasonic or radio frequency energy is applied externally to a subject's body to heat different tissues. This is known as the high intensity focused ultrasonic knife (HIFU) technique. The working principle of the technique is that high-energy ultrasonic waves are emitted without contact and enter a human body via a water medium coupling. The applied energy can be focused to a very small spot within the human body so as to heat the tissues at that spot to a temperature sufficient to create a desired therapeutic effect, and to necrotize tissue at the focal spot within a very short period of time. This technique can be selectively used to destroy unwanted tissues within a body. For example, tumors or other unwanted tissues can be destroyed by applying heat, and the applied heat can heat the abnormal tissues to a temperature sufficient to kill them without damaging normal tissues nearby, with the temperature usually between 60° C. to 80° C. Such a process is commonly referred to as "thermal ablation". Other hyperthermia treatments include selectively heating tissues so as to selectively activate a drug, or to promote some other physiological changes in a selected part of the body of a subject under the treatment. In other therapeutic methods, the applied energy can be used to destroy abnormal objects or deposits within a body such as, for example, in ultrasonic lithotripsy.

Magnetic resonance can be used in medical imaging for diagnostic purposes. In magnetic resonance imaging (MRI) procedures, a body region of the subject to be imaged is subjected to a strong magnetic field. Radio frequency (RF) signals are applied to the tissues of the subject within the imaging volume, and under these conditions, atomic nuclei are excited by the applied radio frequency signals and emit faint radio frequency signals, which are referred to as magnetic resonance signals. By superimposing appropriate gradients on the magnetic field during the procedure, the magnetic resonance signals can be obtained selectively from a limited region, such as a two-dimensional slice of the subject's tissue. The frequency and phase of the signals from different parts of the slice can be made to vary with their positions in the slice. By using this known technique, it is possible to demodulate the signals arising from different parts of the slice, and to deduce from these signals the properties of the tissues at each point of the slice.

Various proposals have been made to use magnetic resonance to monitor and guide medical equipment, particularly during a procedure of applying energy into a body. Certain magnetic resonance procedures are temperature sensitive, so that magnetic resonance data acquired by using these procedures will generate an image in a MRI system, and indicate temperature changes in tissues, so as to accomplish a therapeutic procedure. However, there are always some problems when such medical equipment is used in conjunction with an MRI system. Taking a HIFU treatment device as an example, during the MRI imaging procedure, RF signals are usually transmitted into a human body by a large body coil and this large body coil receives magnetic resonance signals emitted from the human body, and the MRI system makes use of these magnetic resonance signals to generate an image. When using medical equipment such as HIFU which requires very high precision imaging, the signal-to-noise ratio during the imaging by such a large body coil does not meet the requirements (the imaging quality of the body coil is not very high due to the fact that the coil is too large, and the bigger the coil is, the less ideal is the imaging quality). Therefore the local imaging quality is not high. An alternative is to acquire the magnetic resonance signals using a fixed receiving coil (local coil), but there are many restrictions in practical application. Since a fixed coil needs to be placed in HIFU solution in order to receive the magnetic resonance signals emitted from the body, and the fixed coil also needs to be connected to a cable and to transmit the magnetic resonance signals to the MRI processor for imaging, there is the problem of sealing the coil and the cable. Moreover, the need to seal the cable and the fixed coil in turn creates the problem of inconveniency in moving the fixed coil, which further results in a restriction to imaging range. All these problems are difficulties encountered when using the fixed coil.

SUMMARY OF THE INVENTION

An object of the present invention is to provide an apparatus for transmitting magnetic resonance signals in MRI-guided medical equipment that avoids the aforementioned problems.

The above object is achieved in accordance with the present invention in a magnetic resonance (MR) system having a magnetic resonance imaging (MRI) apparatus and MRI-monitored medical equipment, wherein the MRI-monitored medical equipment has an inductive coil built into the equipment that receives magnetic resonance signals from a subject and generates inductive electromagnetic signals according to the received magnetic resonance signals. The magnetic resonance imaging system has at least one reception coil that is positioned externally of the MRI-monitored medical equipment and that is connected to the magnetic resonance imaging system via a cable. The reception coil receives the electromagnetic signals that are generated by the inductive coil that is built into the medical equipment.

The medical equipment can be high intensity focused ultrasonic knife equipment. The high intensity focused ultrasonic knife equipment is placed in liquid in a container, and the inductive coil is sealed and fixed in the liquid in the container.

The connection of the cable to the receiving coil is in a plug-in manner.

The inductive coil can be positioned above the high intensity focused ultrasonic knife equipment, so as to allow the ultrasonic waves emitted by the high intensity focused ultrasonic knife equipment to pass through the plane of the inductive coil vertically.

The inductive coil is placed to avoid the ultrasonic waves emitted by the high intensity focused ultrasonic knife equipment, so as to allow the ultrasonic waves to pass through the central plane of the inductive coil.

An advantage of the present invention is that the compatibility between the MRI system and the medical equipment guided is significantly improved, and the MRI real time detection during a treatment becomes more convenient. The drawbacks in the sealing and fixing of the previous coil and the cable are avoided, and images of a better quality are provided during therapy. Therefore, surgical operation effects of therapeutic equipment, particularly the HIFU equipment, are improved. Furthermore, the present invention is convenient to install, easy to maintain, and the imaging quality and flexibility are improved by the coils of various sizes for detecting corresponding positions, and the simple mechanical devices also reduce malfunction rate.

DESCRIPTION OF THE PREFERRED EMBODIMENTS

The present invention is described in detail with reference to the accompanying drawings.

When magnetic resonance signals are received by using a fixed coil in the current MRI-monitored medical equipment, the coil may need to be sealed or be moved flexibly, at such time an inductive coupling coil can be used to achieve the functions of a fixed coil, and hereinbelow, the detailed construction of the present invention is described with an MRI system-guided HIFU equipment as an example.

Figure 1:
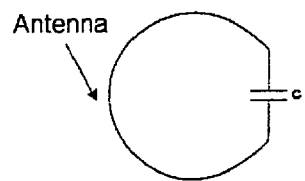
FIG. 1 is a circuit diagram for an embodiment of the inductive coil according to the present invention.
Figure 2:
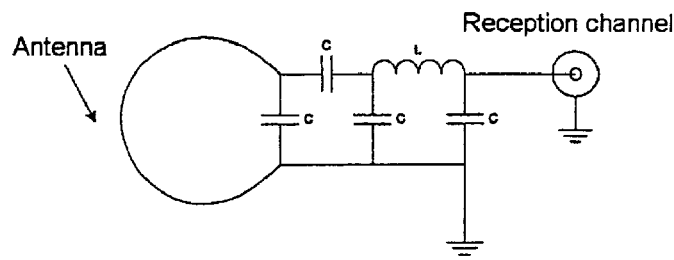
FIG. 2 is a circuit diagram for an embodiment of the receiving coil according to the present invention.

An inductive coupling coil is divided into two parts: an inductive coil (shown in FIG. 1) is a standard LC resonance coil for receiving magnetic resonance signals returning from a human body and generating corresponding inductive electromagnetic waves. The receiving coil is a common coil (shown in FIG. 2) for receiving the electromagnetic wave signals from the inductive coil and transmitting the same to the MRI system via a signal channel. The inductive coil is relatively independent, and can be fixed at any place in a water trough by one-step injection-molding. The best place to position it is just above a HIFU transmitter where the most magnetic resonance signals from a human body can be received. There is no need for connecting to other equipment, and no restriction by a cable, therefore there is no problem in connecting a sealed cable. At the same time the sizes of inductive coils can be tailored and replacement can be selected according to the size of a therapeutic region. The receiving coil is connected by an output cable for the connection to the control portion of the MRI system. Due to the fact that it is far away from the human body that emits the magnetic resonance signals, the reception of the electromagnetic wave signals from the inductive coil will not be disturbed. The position of the receiving coil is not restricted by the HIFU equipment, so it is flexible to place and to move. Therefore the shortcomings in the compatibility of the common RF receiving coils in the HIFU, MRI are solved.

Figure 3:
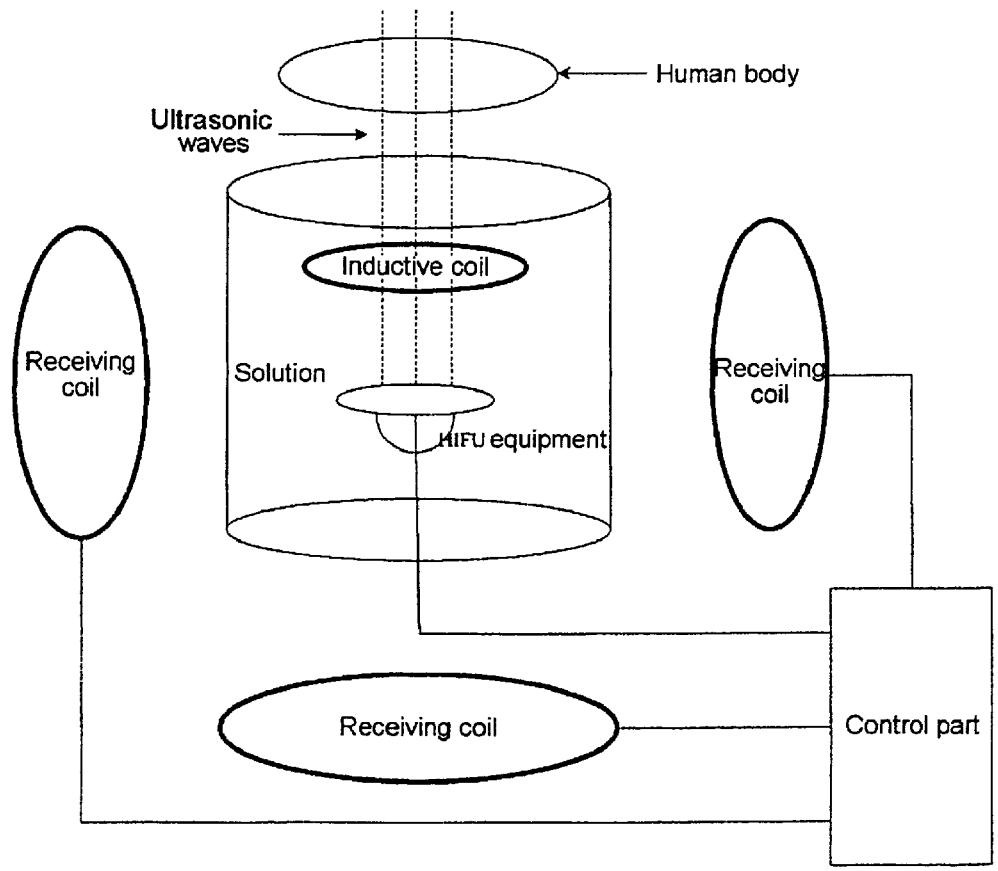
FIG. 3 schematically illustrates an apparatus for transmitting magnetic resonance signals to an MRI system in an embodiment of the present invention with HIFU equipment.

FIG. 3 shows an illustrative view of an apparatus for transmitting magnetic resonance signals to an MRI system in the application of an embodiment of the present invention in HIFU equipment. A human body is positioned just underneath a liquid container with the person's skin of an affected part contacting the surface of the solution, which is preferably an aqueous solution. The inductive coil needs to avoid the emitting pathway of the HIFU equipment. Therefore, in the most preferred embodiment, the ultrasonic waves emitted by the HIFU equipment pass through the central plane of the inductive coil. The cable of the HIFU equipment extends out of the solution to connect to the control unit, which can be a control computer in the MRI system and which controls the HIFU equipment and the inductive coil, as is conventional. The MRI control unit controls the operation of the HIFU device and the transmission of signals by the body coil. The receiving coil is positioned outside the container for receiving the electromagnetic wave signals transmitted by the inductive coil. The receiving coil's cable is connected to the control unit of MRI system, so that the receiving coil can be replaced according to the imaging requirements, so as to improve the imaging quality and the imaging range (allowing the distance for a human body to receive the magnetic resonance signals to be increased). Thus the imaging problem of the MRI system when used with the HIFU technique can be solved. The imaging range may be changed as desired by replacing different receiving coils, and as shown in FIG. 3, the position of the receiving coil can be moved, so the position of the receiving coil can be adjusted according to the needs for imaging, so as to optimized it in order to obtain the maximum magnetic flux in the inductive coil and to produce images of optimal angles and effects.

An advantage of the present invention is that the compatibility between the MRI system and the medical equipment monitored thereby is significantly improved by the present invention, and the MRI real time detection during a treatment becomes more convenient. The drawbacks in the sealing and fixing of the previous coil and the cable are avoided. Images of a better quality are provided during therapy, therefore surgical operation effects of therapeutic equipment, particularly the HIFU equipment, are improved. Furthermore, the present invention is convenient to install, easy to maintain, and the imaging quality and flexibility are improved by the coils of various sizes for detecting corresponding positions, and the simple mechanical devices also reduce malfunction rate.

Although modifications and changes may be suggested by those skilled in the art, it is the intention of the inventors to embody within the patent warranted hereon all changes and modifications as reasonably and properly come within the scope of their contribution to the art.

We claim as our invention:
1. A magnetic resonance (MR) system comprising:
    a magnetic resonance imaging (MRI) apparatus;
    MRI-monitored medical equipment;
    said magnetic resonance imaging apparatus comprising a control unit that monitors said MRI-monitored medical equipment;
    said MRI-monitored medical equipment comprising an inductive coil fixed in said MRI-monitored medical equipment that detects magnetic resonance signals from a subject and radiates electromagnetic signals corresponding to the detected magnetic resonance signals; and
    said magnetic resonance imaging apparatus comprising at least one receiving coil positioned externally of said MRI-monitored medical equipment, said at least one receiving coil being connected to said control unit via a cable, and said receiving coil being inductively coupled with said inductive coil and receiving said electromagnetic signals wirelessly radiated by said inductive coil of said MRI-monitored medical equipment and supplying the received electromagnetic signals to the control unit.
2. A system as claimed in claim 1 wherein said MRI-monitored medical equipment comprises high intensity focused ultrasound knife equipment, said high intensity focused ultrasound knife equipment being disposed in a liq- uid in a container, and said inductive coil being sealed and fixed in the liquid in said container.

3. A system as claimed in claim 2 wherein said inductive coil is a planar coil disposed in a plane, and wherein said inductive coil is disposed above said high intensity focused ultrasound knife equipment and is oriented to cause ultrasonic waves emitted by said high intensity focused ultrasound knife equipment to proceed vertically through said plane.

4. A system as claimed in claim 3 wherein inductive coil is positioned to avoid interaction by said inductive coil with said ultrasonic waves by being oriented so that said ultrasonic waves pass through a central region of said plane of said inductive coil.

5. A system as claimed in claim 1 comprising a plug-in connection connecting said cable to said receiving coil.

* * * * *